(12) United States Patent
Agrawal et al.

(10) Patent No.: US 8,200,589 B2
(45) Date of Patent: Jun. 12, 2012

(54) SYSTEM AND METHOD FOR NETWORK ASSOCIATION INFERENCE, VALIDATION AND PRUNING BASED ON INTEGRATED CONSTRAINTS FROM DIVERSE DATA

(75) Inventors: Amit Agrawal, Pune (IN); Rohit Vaishampayan, Pune (IN); Ashutosh, Pune (IN)

(73) Assignee: Persistent Systems Limited, Pune (IN)

( * ) Notice: Subject to any disclaimer, the term of this patent is extended or adjusted under 35 U.S.C. 154(b) by 633 days.

(21) Appl. No.: 12/374,759

(22) PCT Filed: Jul. 25, 2007

(86) PCT No.: PCT/IN2007/000316
§ 371 (c)(1),
(2), (4) Date: Jan. 22, 2009

(87) PCT Pub. No.: WO2008/047383
PCT Pub. Date: Apr. 24, 2008

(65) Prior Publication Data
US 2009/0187525 A1    Jul. 23, 2009

(30) Foreign Application Priority Data
Jul. 28, 2006    (IN) .......................... 1194/MUM/2006

(51) Int. Cl.
*G06F 15/18* (2006.01)
*G06N 3/00* (2006.01)
*G06N 3/12* (2006.01)
(52) U.S. Cl. ........................................................ 706/13

(58) Field of Classification Search .................... 706/13
See application file for complete search history.

(56) References Cited

U.S. PATENT DOCUMENTS

| | | | |
|---|---|---|---|
| 6,324,533 B1 | 11/2001 | Agrawal et al. | |
| 6,430,547 B1 | 8/2002 | Busche et al. | |
| 6,957,214 B2 | 10/2005 | Silberberg et al. | |
| 6,983,227 B1 | 1/2006 | Thalhammer-Reyero | |
| 6,990,238 B1 | 1/2006 | Saffer et al. | |
| 7,024,417 B1 | 4/2006 | Russakovsky et al. | |
| 2003/0161266 A1 | 8/2003 | Baccelli et al. | |
| 2004/0132108 A1* | 7/2004 | Hupp et al. | 435/7.2 |
| 2005/0260663 A1* | 11/2005 | Solomon | 435/6 |

OTHER PUBLICATIONS

Handley, Simon. "Predicting Whether or Not a Nucleic Acid Sequence is an *E. Coli* promoter Region using Genetic Programming" IEEE, 1995. [Online] DOwnloaded Sep. 8, 2011. http://ieeexplore.ieee.org/stamp/stamp.jsp?tp=&arnumber=404270.*

* cited by examiner

*Primary Examiner* — Kakali Chaki
*Assistant Examiner* — Ben Rifkin
(74) *Attorney, Agent, or Firm* — Foley & Lardner LLP

(57) ABSTRACT

A network inference and validation engine is presented which combines data of different types into a network associations' inference and performs validation of existing networks based on constraints from several data sets or previously known linkages. The engine would assist scientists to integrate information from various sources into a network of association, validate previously known associations against the supplied constraint data sets and prune or modify existing connections based on subsequent experiments.

12 Claims, 4 Drawing Sheets

SYSTEM AND METHOD FOR NETWORK ASSOCIATION INFERENCE, VALIDATION AND PRUNING BASED ON INTEGRATED CONSTRAINTS FROM DIVERSE DATA

INTRODUCTION

The present invention relates to interpreting the information contained in these data sets and to combine various aspects captured into a technologically usable knowledge.

More particularly, a network association mining algorithm and associated methods which accepts data from biological and other experiments and automatically produces a network model.

Still particularly, the network association mining algorithm and associated methods which attempts to explain the behaviour of the biological or other system underlying the data using evolutionary techniques.

This invention relates to modern experiments generate voluminous data capturing diverse aspects of complex phenomena. Modern experiments generate voluminous data capturing diverse aspects of complex phenomena. To deal with the problem of interpreting the information contained in these data sets and to combine various aspects captured into a technologically usable knowledge, something of a paradigm shift has emerged in recent times. This new paradigm relies on ability to form multiple competing hypotheses based on the observed data, the ability to validate or rule out multiple hypotheses at the same time and the ability to do it in an automatic way with minimal human intervention. Networks of relationships between different data entities of interest and computational representations of such networks are fast becoming a corner stone of such approaches. The representation of the phenomena in terms of networks has the advantage of data reduction and these networks help in uncovering underlying processes at work, resulting in increased insight and better technological applications. Consequently, network analysis has become widely applicable methodology in applications to understand financial, social, physical or biological data and have helped understanding these very complex relationships.

Furthermore, many experiments or observations are carried out to capture different facets of a underlying, possibly complex process. Each observation results in a data set which captures some information about the network of associations. Such data sets may contain independent, complementary or sometimes even conflicting information about the process. The conflict may come due to variations in experimental conditions or apparatuses, noise or random fluctuations or may even be inherent in the nature of experiments. If the underlying process is hierarchic in nature, then there may be a number of experiments, with each giving information about a different level of hierarchy. It is of importance to be able to extract as much of relevant information as possible from all the data available and construct a network of associations.

Furthermore, depending on the context, one or the other of the data sets may be more reliable than the others. Thus information gleaned from each may not be of the same weightage. While combining the information, one may wish to take into account the particular weights assigned to each of the data sets depending on the context.

Another issue is the validation of a given inference against data obtained by a repetition of similar experiment or from other experiments and even from prior knowledge.

PRIOR ART

A U.S. Pat. No. 6,990,238 claims, A computer-implemented method for simultaneous visualization of disparate data types, the method comprising: (1) selecting a set of attributes associated with an object, the attributes selected comprising a text data type and one other data type chosen from a biopolymer sequence data type, a numerical data type, and a categorical data type; (2) creating a high dimensional vector representing the object by applying transformation operations to the selected attributes; and (3) projecting the high dimensional vector thereby visualizing the object based on the attributes selected;

wherein the transformation operations for the attributes of the text data type comprise: (a) semantically filtering a set of documents in a database to extract a set of semantic concepts, to improve an efficiency of a predictive relationship to its content, based on at least one of word frequency, overlap and topicality;

(b) defining a topic set, said topic set being characterized as the set of semantic concepts which best discriminate the content of the documents containing them, said topic set being defined based on at least one of word frequency, overlap and topicality; (c) forming a matrix with the semantic concepts contained within the topic set defining one dimension of said matrix and the semantic concepts contained within the filtered set of documents comprising another dimension of said matrix; (d) calculating matrix entries as the conditional probability that a document in the database will contain each semantic concept in the topic set given that it contains each semantic concept in the filtered set of documents; and (e) providing said matrix entries from step (d) for creating the high dimensional vector.

The U.S. Pat. No. 6,957,214 further claims, "A computer-implemented system for accessing information from a plurality of distributed and heterogeneous data sources each having a plurality of users and applications with a plurality of domain perspectives, the architecture comprising: a user domain module operable to act as an interface with the users and the applications by translating queries from the users and the applications into a form recognizable by an aggregation domain module and by receiving responses from the aggregation domain module and translating the responses into a form recognizable by the users and applications; a generic domain data model operable to receive translated queries from the user domain module, translate the queries into a form recognizable to a data source domain module, receive responses from the data source domain module, translate the responses into a form recognizable by the user domain module, and transmit the translated responses to the user domain module; and a data source domain module operable to receive the translated queries from the aggregation domain module, identify target data sources to transmit the queries to, translate the queries specific to the identified data sources, receive responses from the identified data sources, translate the responses, and transmit the translated responses to the aggregation domain module; and a knowledge base comprising a data model of the generic domain, data models of each data source, conceptual terminology translations between the user domains and the generic domain and conceptual terminology translations between the generic domain and the data sources.

The U.S. Pat. No. 6,430,547 further claims, A method for determining data relationships of physical sample data and remotely sensed data within a region, the method comprising the computer-implemented steps of: identifying locations of physical samples within the region; recording data associated with physical characteristics of the physical samples; identifying locations for obtaining remotely sensed data within the region; recording remotely sensed data; and associating the locations of physical samples within the region with the locations of remotely sensed data to form a set of spatial relationships.

The U.S. Pat. No. 6,324,533 further claims, "A method for mining rules from an integrated database and data-mining system having a table of data transactions and a query engine, the method comprising the steps of:
a) performing a group-by query on the transaction table to generate a set of frequent 1-itemsets;
b) determining frequent 2-itemsets from the frequent 1-itemsets and the transaction table;
c) generating a candidate set of (n+2)-itemsets from the frequent (n+1)-itemsets, where n=1;
d) determining frequent (n+2)-itemsets from the candidate set of (n+2)-itemsets and the transaction table using a query operation;
e) repeating steps (c) and (d) with n=n+1 until the candidate set is empty; and
f) generating rules from the union of the determined frequent itemsets.

The U.S. Pat. No. 7,024,417 further claims, "A method for data mining using an algorithm, the algorithm having a build task, a test task, and an apply task, each task having a number of parameters, each parameter having a type, the method comprising: retrieving a signature associated with the algorithm, said signature including, for the build task, the number of parameters and the type of each parameter associated with said task, as well as an information field for each parameter associated with said task,
said information field indicating the meaning and/or recommended usage of said parameter, said signature also including, for the build task, one or more coefficients for the algorithm; and creating a template for said the build task based on said signature,
said template indicating one or more of said parameters that need to be initialized by a user to invoke said task and one or more model values that are to be derived from a data set; and executing said template to create a mapping between said one or more coefficients and said one or more model values.

The U.S. Pat. No. 6,983,227 claims "A computer based virtual models of complex systems, together with integrated systems and methods provide a development and execution framework for visual modeling and dynamic simulation of said models. The virtual models can be used for analysis, monitoring, or control of the operation of the complex systems modeled, as well as for information retrieval. More particularly, the virtual models in the present implementation relate to biological complex systems. In the current implementation the virtual models comprise building blocks representing physical, chemical, or biological processes, the pools of entities that participate in those processes, a hierarchy of compartments representing time-intervals or the spatial and/or functional structure of the complex system in which said entities are located and said processes take place, and the description of the composition of those entities. The building blocks encapsulate in different layers the information, data, and a mathematical model that characterize and define each virtual model, and a plurality of methods is associated with their components. The models are built by linking instances of the building blocks in a predefined way, which, when integrated by the methods provided in this invention, result in multidimensional networks of pathways. A number of functions and graphical interfaces can be selected for said instances of building blocks, to extract in various forms the information contained in said models. Those functions include: a) on-the-fly creation of displays of interactive multidimensional networks of pathways, according to user selections; b) dynamic quantitative simulations of selected networks; and c) complex predefined queries based on the relative position of pools of entities in the pathways, the role that the pools play in different processes, the location in selected compartments, and/or the structural components of the entities of those pools. The system integrates inferential control with quantitative and scaled simulation methods, and provides a variety of alternatives to deal with complex dynamic systems and with incomplete and constantly evolving information and data.

These prior art algorithms and associated methods are different from the proposed invention for the development of high quality System and Method for Inferring a Network of Associations by integrating diverse type of data and for validating and pruning previous known networks based on constraints by other data sets.

The present invention utilises the fitness criteria to flexibly integrate different types of data into the inference. The fitness criteria make it flexible and allow for tuning of the relative weights of different data sets to be specified according to convenience or confidence in a particular data source. The present invention is also capable of producing a population of models simultaneously, each model differing slightly from each other therefore allowing the possibility of experimenting with fluctuating or imprecise data in primary or secondary sets. The present invention allows one to swap primary and secondary data sets thereby providing different views of integrated inference. Furthermore the present invention does not require voluminous amount of training corpus (e.g. as in some artificial neural networks) and instead works only with the specified data set(s). The invention also does not require predefined configuration of various entities in the network and instead is capable of inferring such configuration and topology.

This invention thus seeks to overcome the limitations of the prior art.

The object of this invention is to provide for a network inference and validation engine which would combines data of different types into a network association's inference and performs validation of existing networks based on constraints from several data sets or previously known linkages.

Another object of this invention is to provide a network of relationships between different data entities of interest and computational representations of such networks.

| Name | Name description |
| --- | --- |
| CDC27 | cell division cycle |
| CLN1 | cyclin |
| CLN2 | cyclin |
| SWI4 | SWItching deficient |
| CLN3 | cyclin |

-continued

| Name | Name description |
|---|---|
| MBP1 | MluI-box Binding(cell cycle) |
| CLB5 | CycLin B |
| MCM2 | MiniChromosome Maintenance |
| CDC20 | cell division cycle |
| CLB6 | CycLin B |
| SIC1 | Substrate/Subunit Inhibitor of Cyclin-dependent protein kinase |
| CDC28 | cell division cycle |
| SWI6 | SWItching deficient |
| PHO85 | PHOsphate metabolism |
| PCL2 | PHO85 CycLin |
| CDC53 | cell division cycle |
| CDC4 | cell division cycle |
| ORC2 | Origin Recognition Complex |
| GRR1 | Glucose Repression-Resistant |
| CDC6 | cell division cycle |
| FAR1 | Factor Arrest |
| FUS3 | cell FUSion |
| CDC45 | cell division cycle |

The mapping between the block numbers and the names is given below.

| Block | Name |
|---|---|
| 201 | CDC27 |
| 202 | CLN1 |
| 203 | CLN2 |
| 204 | SWI4 |
| 205 | CLN3 |
| 206 | MBP1 |
| 207 | CLB5 |
| 208 | MCM2 |
| 209 | CDC20 |
| 210 | CLB6 |
| 211 | SIC1 |
| 212 | CDC28 |
| 213 | SWI6 |
| 214 | PHO85 |
| 215 | PCL2 |
| 216 | CDC53 |
| 217 | CDC4 |
| 218 | ORC2 |
| 219 | GRR1 |
| 220 | CDC6 |
| 221 | FAR1 |
| 222 | FUS3 |
| 223 | CDC45 |

Figure 1:
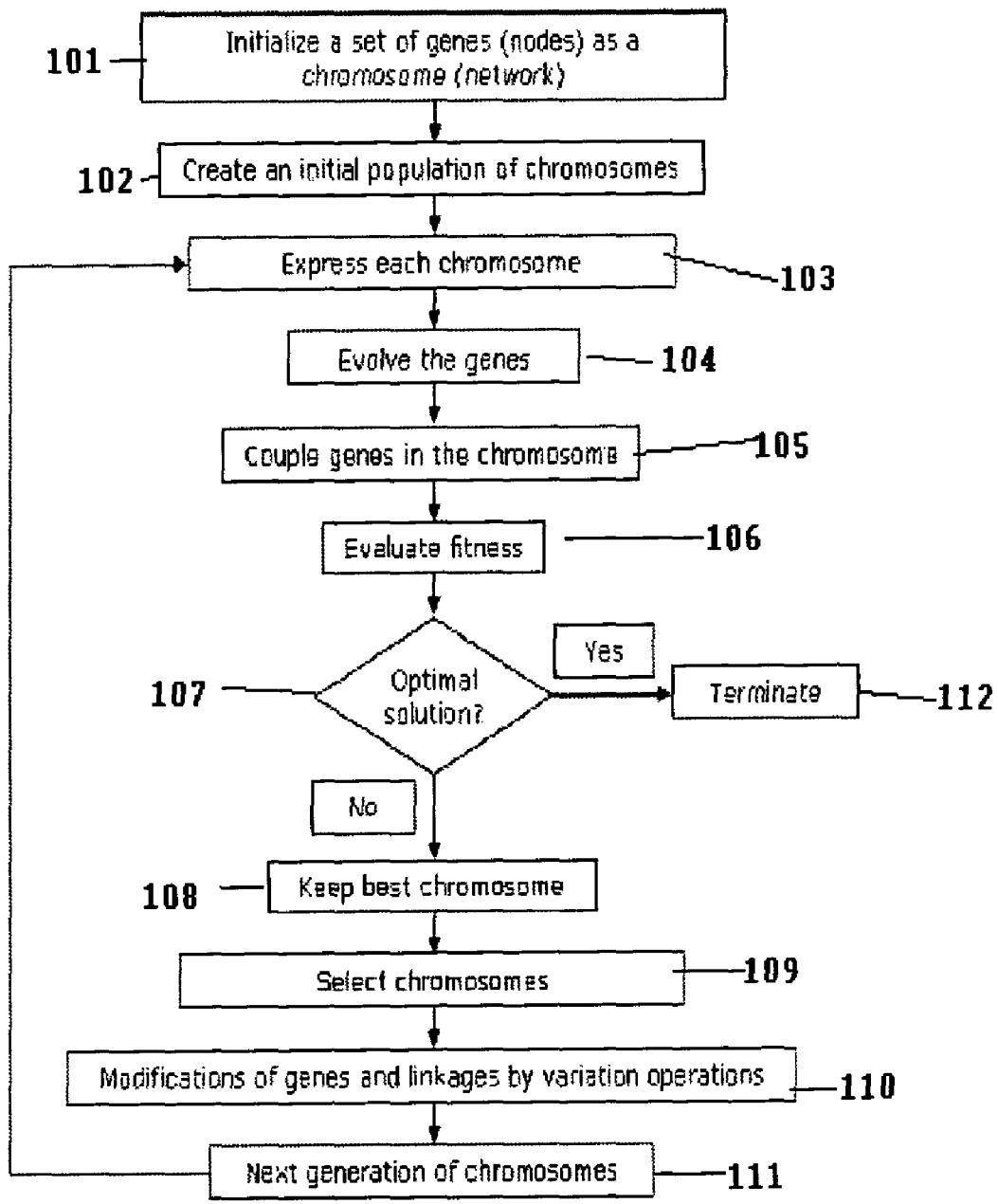
FIG. 1: The Flow for the Evolutionary Algorithm: A flowchart showing the operation of the inference algorithm in accordance with the embodiment of the invention
Figure 2A:
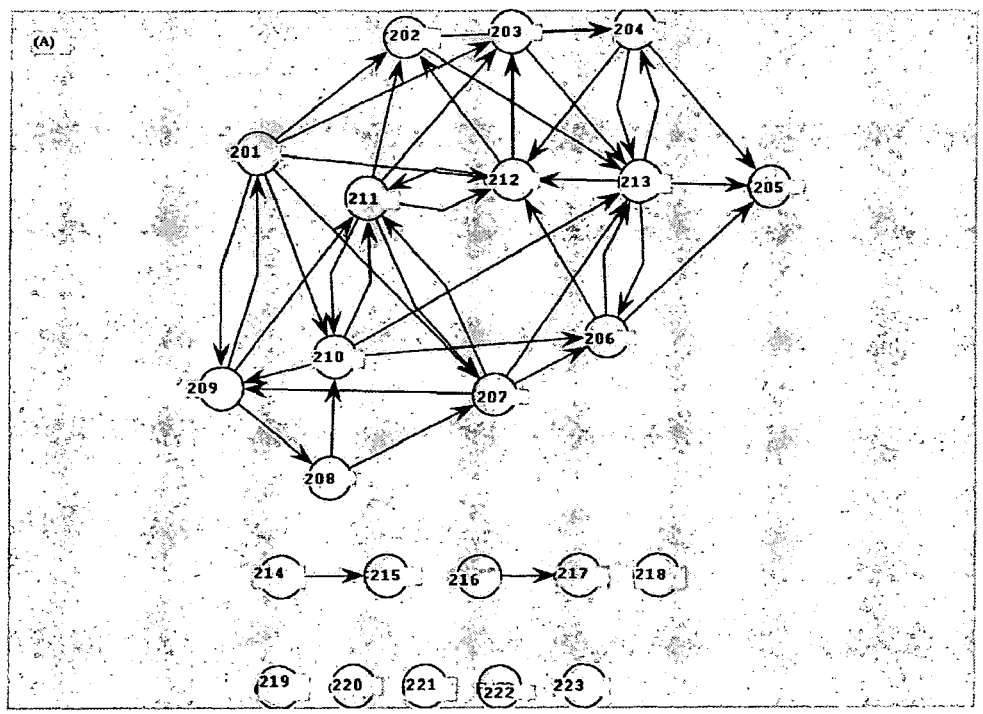
FIG. 2A: Network from a single experiment: CHIP (Chromatin Immuno-precipitation) chip on Yeast Cell cycle genes This is a directed network where the arrows between spherical nodes denote the associations and the directed of the association. the descriptions of various names used is
Figure 2B:
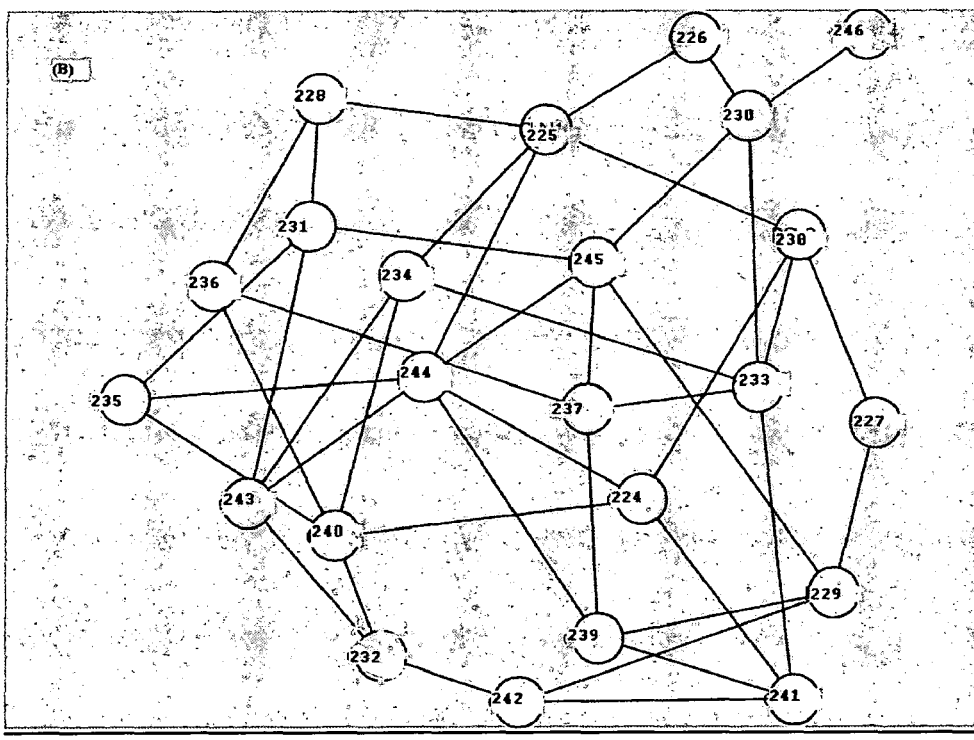
FIG. 2: denotes example networks obtained from datasets of single experiments of diverse types as listed below.

FIG. 2B: Example Network from a single experiment: Mutual information based network on expression dataset The mapping between the block numbers and the names is given below.

| 224 | CDC27 |
|---|---|
| 225 | CLN1 |
| 226 | CLN2 |
| 227 | SWI4 |
| 228 | CLN3 |
| 229 | MBP1 |
| 230 | CLB5 |
| 231 | MCM2 |
| 232 | CDC20 |
| 233 | CLB6 |
| 234 | SIC1 |
| 235 | CDC28 |
| 236 | SWI6 |
| 237 | PHO85 |
| 238 | PCL2 |
| 239 | CDC53 |
| 240 | CDC4 |

-continued

| 241 | ORC2 |
|---|---|
| 242 | GRR1 |
| 243 | CDC6 |
| 244 | FAR1 |
| 245 | FUS3 |
| 246 | CDC45 |

Figure 2C:
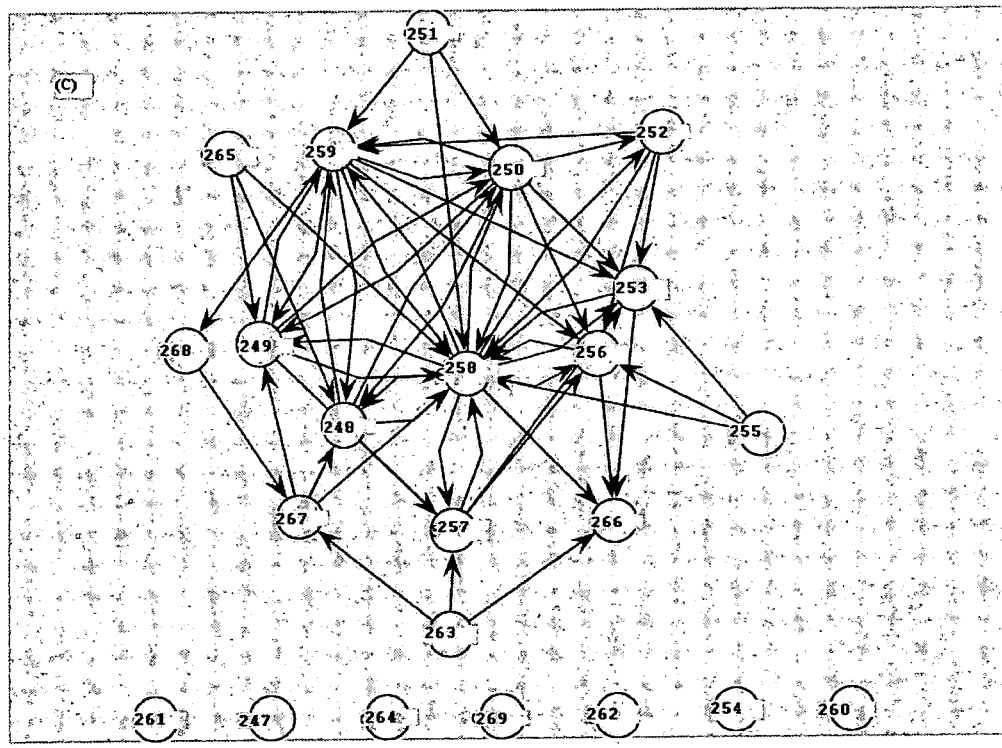

FIG. 2C: Example Network formed from partial pathway information. The mapping between the block numbers and the names is given below

| 247 | CDC27 |
|---|---|
| 248 | CLN1 |
| 249 | CLN2 |
| 250 | SWI4 |
| 251 | CLN3 |
| 252 | MBP1 |
| 253 | CLB5 |
| 254 | MCM2 |
| 255 | CDC20 |
| 256 | CLB6 |
| 257 | SIC1 |
| 258 | CDC28 |
| 259 | SWI6 |
| 260 | PHO85 |
| 261 | PCL2 |
| 262 | CDC53 |
| 263 | CDC4 |
| 264 | ORC2 |
| 265 | GRR1 |
| 266 | CDC6 |
| 267 | FAR1 |
| 268 | FUS3 |
| 269 | CDC45 |

Figure 2D:
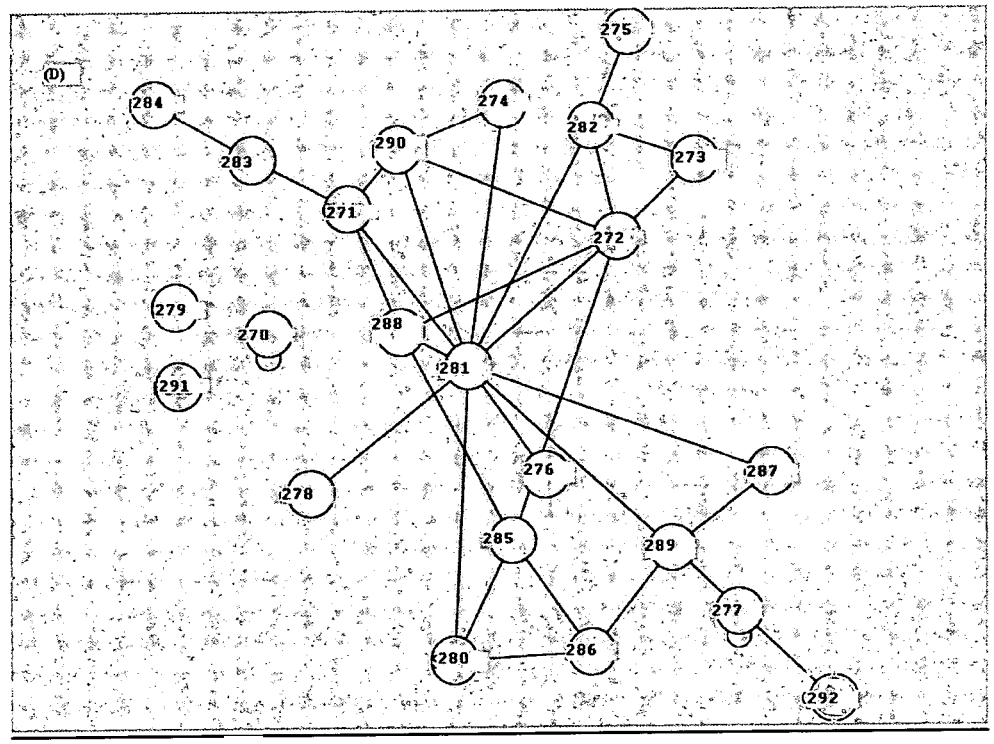

FIG. 2D: Example Network from Protein-Protein interaction data

| 270 | CDC27 |
|---|---|
| 271 | CLN1 |
| 272 | CLN2 |
| 273 | SWI4 |
| 274 | CLN3 |
| 275 | MBP1 |
| 276 | CLB5 |
| 277 | MCM2 |
| 278 | CDC20 |
| 279 | CLB6 |
| 280 | SIC1 |
| 281 | CDC28 |
| 282 | SWI6 |
| 283 | PHO85 |
| 284 | PCL2 |
| 285 | CDC53 |
| 286 | CDC4 |
| 287 | ORC2 |
| 288 | GRR1 |
| 289 | CDC6 |
| 290 | FAR1 |
| 291 | FUS3 |
| 292 | CDC45 |

Figure 3:
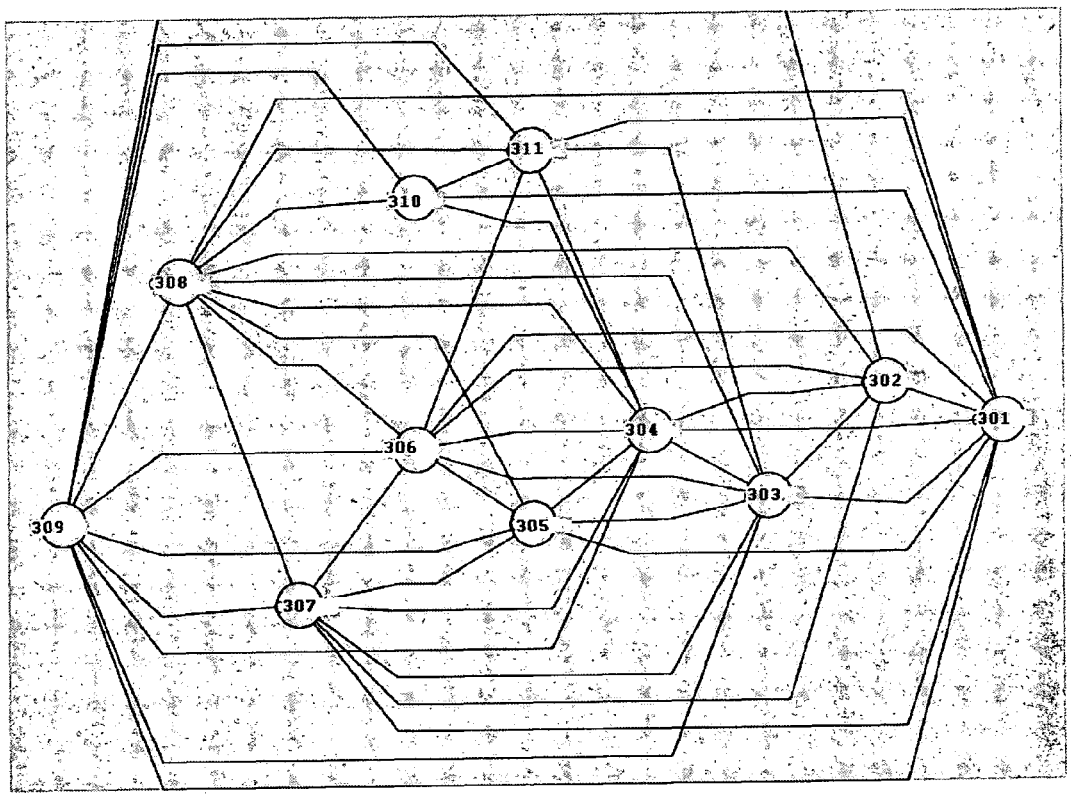

FIG. 3: Hierarchically ordered Network obtained from combining data sets in FIG. 2 A),B),C),D) (secondary data sets) with gene expression profiles with time as parameter as primary dataset.

| 301 | CDC28 |
|---|---|
| 302 | CLN1 |
| 303 | CLN2 |

-continued

| 304 | SIC1 |
| --- | --- |
| 305 | CLB5 |
| 306 | CDC20 |
| 307 | CDC4 |
| 308 | CDC27 |
| 309 | MCM2 |
| 310 | GRR1 |
| 311 | CLB6 |

SUMMARY OF THE INVENTION

It is assumed that the underlying process for the network formation can be modelled as a system of coupled dynamical systems, each dynamical system is described by a state vector x(t) In our model the state corresponds to the expression level of a gene at a given time t. This state could be dependent on values of other data entities.

Thus the network consists of a collection of N dynamical systems characterized by a state vector $$x = (x1 x2 \ldots xj) j <= N$$

The state of system is updated, synchronously or asynchronously, by an evolution rule or local dynamics. This evolution rule can be continuous or discrete. Each node representing the data entity can have a different local dynamics, i.e.

$$\dot{x}_i = f_i(x_k(t), \mu)$$

$$x_i^{n+1} = f(x_k^n, \mu)$$

Where xk denotes the state vector (x1 ... xk) and I runs from 1 to N the parameter vector □ denotes the parameters that can influence the local dynamics.

These dynamical systems are coupled together in a network whose topology is given by a matrix Wik No assumptions are made about the nature of coupling (i.e. no assumptions like nearest or next nearest neighbor couplings global or mean field coupling etc.).

$$x_i(t+1) = \left(1 - \frac{\epsilon_{ii}}{N}\right) f_i^l(x_i) + \frac{1}{N} \sum_k \epsilon_{ik} W_{ik} f_k^p(x_k)$$

denotes the dynamics of the whole network, where □i is a parameter matrix representing the coupling strengths of respective edges in the network.

Thus in the model, the genes influence each other in two ways: though the function fi, which we call direct influence and through the coupling term in the equation which we refer to as indirect influence. The indirect influence is useful in a number of different situations. The data from the experiments is many times noisy and error prone. Also, also usually a number of experiments are averaged to produce a time course profile. Due to these factors, a variable which should appear in the direct influence is not sometimes detected i.e. averaging or noise may mask the effect of a variable.

The indirect influence allows one to incorporate effects of such "left out" variable. Thus there are a number of unknown that we want to infer from the data. The form of each of the functions is unknown, as are the parameters governing the equations. The connection matrix and the coupling weight matrix are also unknowns. To reduce the number of unknowns, in the remaining discussion below we would be concentrating on unweighted networks in which all edges have equal weights and thus we can replace the matrix by a constant. This is the only free parameter in our system. The downside of this is that we have to check for the variation of behavior with respect to this parameter. This can be done either numerically or analytically by considering the bifurcation structure of the network dynamical system with this parameter. Towards this aim we techniques from stability analysis of dynamical system. The aim of such an exercise is to find the optimum parameter value for the given data set and then fix the value at this value.

It is also instructive to look at the stability of the networks from another angle.

The networks that occur in nature have to preserve their function in face of random perturbation to variables as well as parameters. Thus the networks that are inferred should be robust to such variation and should have good stability properties. To tackle the problem of inferring a large number of unknowns from a finite, and often short time profile data we use an evolutionary algorithm.

Due to their stochastic nature, evolutionary algorithms are often the best (and sometimes the only) option to deal with incomplete data. This is possible mainly because the stochasticity is theoretically capable of generating all possible configurations (including effects of hidden variable and uncertainty) and if the selection mechanism is robust and targeted we can zero down to the vicinity of true solution reasonably fast. An evolutionary algorithm indicates a subset of evolutionary computation, which is a part of artificial intelligence. It is a generic term used to indicate any population-based metaheuristic optimization algorithm that uses mechanisms inspired by biological evolution, such as reproduction, mutation, recombination, natural selection and survival of the fittest. Candidate solutions to the optimization problem play the role of individuals in a population, and the cost function determines the environment within which the solutions "live". Evolution of the population then takes place after the repeated application of the above operators.

In essence the Evolutionary algorithms occupy a particular place in the hierarchy of stochastic optimization methods. This hierarchy has evolved over time from Monte-Carlo, Metropolis Stein and Stein (MSS) algorithms to simulated annealing, evolutionary strategies and then onto genetic algorithms and genetic programming. While the inspiration and metaphors for the earlier algorithms came from the domain of physical processes, later on more and more biological processes have been increasingly used. This hierarchy can be progressively described as follows:

(1) Monte-Carlo Methods

This was one of the earliest approaches in stochastic optimization. Random solutions are generated and only a subset of them is accepted based on some criterion (e.g. value of a random configuration). Selecting random solutions allows one to explore the search space widely and hence drive the system towards desired solution. However, since there is no fine tuning of acceptability criterion, this method can be slow when there are multiple solutions possible which are widely distributed in search space.

(2) Simulated Annealing

To refine the acceptability criterion a notion of suitably defined "energy" and "temperature" was introduced. The acceptable solution is the one among the randomly selected solutions, as in Monte Carlo, which, in addition, also minimizes the energy of the system. In essence the algorithm is a stochastic steepest descent method which finds global minima.

(3) Evolutionary Strategies

This was the first evolutionary algorithm where the notion of a population was introduced. The solutions among this population are accepted by some heuristic criterion (such as one fifth success rate), The concept of randomly changing the solution mutation was introduced here.

(4) Genetic Algorithms

Genetic algorithms improved the Evolutionary Strategies approach by introducing two powerful notions. One was that of applying a cross over operator to diversify the population and second was to represent the population as a collection of strings. In addition it generalized the acceptability criteria from a heuristic one fifth rule to a more generic kind i.e. a fitness function.

(5) Genetic Programming

This was the first approach in which the solutions are selected not based on their structural representation but based on their applicability. In other words, the fitness of the individuals is not determined by its structural representation, but by the behaviour of the structural representation. This kind of behaviour is obtained by representing the population as trees of computational modules and actually evaluating the result of such computation.

(6) Genotype-Phenotype Based Programming

The next step in using biological metaphors for evolutionary computing is separation on the structural representations i.e. Genotypes from their behaviour Phenotype. While genetic algorithms deal directly with genotypes and genetic programming deals directly with phenotypes, it is instructive to evolve the two populations simultaneously. This offers the possibility of diversifying and selecting the string populations and obtaining fitness bounds on phenotypes. Examples of such approaches are GEP, MEP and AIS.

Because they do not make any assumption about the underlying fitness landscape, it is generally believed that evolutionary algorithms perform consistently well across all types of problems. This is evidenced by their success in fields as diverse as engineering, art, biology, economics, genetics, operations research, robotics, social sciences, physics and chemistry.

The current algorithm is based on the separation of genotype/phenotype mechanisms. An initial population of chromosomes is evolved by applying the genetic operators and fitness of the individual is evaluated by expressing it. This expression is done in form of (multiple) trees. Thus the fitness criterion operates on the trees while the genetic operations are applied on the chromosomes. The expressed trees and sub-trees can have various degree of complexity thus allowing one to handle objects with various levels of complexity with the same chromosome. Each chromosome can be composed of multiple genes thus allowing one to break up a given problem in sub parts and evolve these parts simultaneously.

The genes are strings whose characters can represent terminals as well as operators. The operators can be mathematical or logical functions. Multiple genes are linked together by a linking function which can be a mathematical or logical function. The genetic operators in are mutation, transposition, recombination, gene recombination, insertion sequence transposition, root transposition. A greater number of genetic operators allows for continuous infusion of new individuals into the population. This results in a better success rate with evolutionary time. Due to the particular structure of genes the resulting trees are always valid and thus no effort is needed in validation. The nodes of the tree represent the operators and the leaves represent the terminals.

We allow the selection by a number of sampling methods including roulette wheel sampling and selection via replacement. An amount of elitism, where a number of best individuals are always carried over to the next population is incorporated. This fraction is determined by an external parameter. Each tree is evaluated to obtain a difference or a differential equation and resultant equation provides the local dynamics of the node.

The fitness function that determines the survival of an individual is actually the core of any evolutionary algorithm. This function critically determines the performance, the convergence and the outcome of the algorithm. The current invention incorporates a novel fitness function which can accommodate a wide variety of factors such as goodness of fit to a given data set, stability of the inferred networks, different types of correlations present in the data, weights given to known prevalent motifs in the networks, contributions from other types of data or experiments on the same problem and incorporation of prior knowledge. The general form of the fitness function is thus:

$$F(\text{network}) = F_{err}(\text{network}) + F_{motif}(\text{network}) + F_{corr}(W_{ij}) + F(\text{prior})(W_{ij}) + F_{s_1}(J_{ij}) + F_{s_2}(J_{ij})$$

Where Ferr denotes the fitness contribution due to the goodness of fit data, Fmotif is the contribution depending on how many prevalent motifs are found in the network, Fcorr is the contribution from correlations (longitudinal or transverse), Fprior is the fitness weightage assigned by prior knowledge.

The prior knowledge can include contributions from other data sets (of the same type or from different experiments). Fs1 and Fs2 are contributions from two stability measures obtained from the network. A particular form of fitness function used for a given problem can include a configuration of one or more of these terms.

For example we can have the following choices $$F_{err}(\text{network}) = \sum_{k=1}^{T} \sum_{i=1}^{n} e^{\sqrt{\frac{(x_{calculated}(t_k) - x_{observed}(t_k))^2}{n}}}$$

$$F_{corr}(W) = \sum_{ij} \delta(W_{ij} - R_{ij})(R_{ij} - T^*)$$

Where □ is the Dirac delta function, T* is the correlation cutoff threshold and $$R_{ij} = \sqrt{\frac{\left[\sum_{t=1}^{N}(X_{it} - \overline{X}_i) \cdot (X_{jt} - \overline{X}_j)\right]^2}{\sum_{t=1}^{N}(X_{it} - \overline{X}_i)^2 \sum_{t=1}^{N}(X_{it} - \overline{X}_i)^2}}$$

The prior knowledge can be incorporated by incorporating it as connections in the weight matrix $$F_{corr}(W) = \sum_{ij} \delta(W_{ij} - P_{ij})$$

Where $P_{ij}$ is a weight matrix incorporating effect of other data sets (of the same type or different) and could itself be obtained from a weighted composition of a number of constituents. For example, for genetic networks this could be Pij=a*Pij (gene expression)+ b*Pij (CHIP data)+c*Pij (Protein-Protein interaction)+ d*Pij (pathway information)+e*Pij (mutual information)+ f*Pij (known literature)

The stability contributions are $$S_1 = \gamma_{l_1} - \gamma_{l_2}$$
$$S_2 = \frac{\gamma l_1 - \gamma s}{\gamma l_2 - \gamma s}$$

Where $\gamma_{l_1}-\gamma_{l_2}$ is a measure of the Geshkorin disk and Jij is the Jacobian matrix of the network dynamics.

We find and characterize communities in the inferred network. Most real networks typically contain parts in which the nodes (units) are more highly connected to each other than to the rest of the network. The sets of such nodes are usually called clusters, communities, cohesive groups, or modules, having no widely accepted, unique definition. Yet it is known that the presence of communities in networks is a signature of the hierarchical nature of complex systems. In this method all cliques, i.e. complete subgraphs of the network are first found. Once the cliques are located, the clique-clique overlap matrix is prepared. In this symmetric matrix each row (and column) represents a clique and the matrix elements are equal to the number of common nodes between the corresponding two cliques, and the diagonal entries are equal to the size of the clique. The k-clique-communities for a given value of k are equivalent to such connected clique components in which the neighboring cliques are linked to each other by at least k-1 common nodes. The communities provide us with nodes of specific interest linked together as well as with the critical nodes which separate two or more communities.

Combining Different Data Sources:

As an example we illustrate with combining data sets for inference of a genetic network.

We take a gene expression time series data set as our primary data set i.e. the data set we want to infer a association network on or the data set that we have the most confidence in. The time series data set is arranged in a form of a matrix, where rows represent the genes involved in the experiment, and column comprises the actual time steps for which the gene expression recordings were taken. Each row of this matrix consequently represents the change in the expression profile of a particular gene for a given series of time steps. Each column of this matrix represents the expression profiles of the involved genes at a particular time point.

There are a number of other experiments/data sets which can help us in elucidating this network. These include interaction between DNA and Proteins e.g. Chromatin Immunoprecipitation {abbreviated as chromatin IP or CHIP} the promoter segments bound by a specific transcription factor are purified and amplified. Chromosomal DNAs which are bound by DNA-binding proteins are cleaved into small fragments. The target promoters of a transcription factor are purified by immunoprecipitation using the specific antibody to the DNA-binding protein. These promoters are then amplified by PCR and measured by high throughput DNA microarrays. The measurement is compared to the background reading in control experiments where immunoprecipitation does not take place. Protein-Protein Interactions can also influence transcription regulation via at least two mechanisms. A protein may chemically modify another protein and propagate the information of gene regulation by protein modification, or it may bind to other proteins to form a complex and carry out a specific function. Both mechanisms may also occur simultaneously on a protein-protein interaction. Various techniques have been developed to detect pair wise interactions of proteins. These methods include yeast two-hybrid systems, co-immunoprecipitation and mass spectrometry. Other source include sequence information, available pathway information or available information about linkages from prior knowledge or literature. We call these data sets secondary data sets Our methodology is based on learning of the gene regulatory network by using a system of differential/difference equation as a model. We deal with an arbitrary form in the right hand side of differential/difference equation to allow flexibility of the model. In order to identify the system of differential/difference equations, we evolve the right hand side of the equations from the time series of the gene's expression.

The right hand side of the equations is encoded in the chromosome. A population of such n geneic chromosomes is created initially. Each chromosome contains a set of n trees, i.e. an n-tuple of trees, where n is the number of genes involved in the experiment. Each chromosome in the population is expressed as an expression tree (ET) for arithmetic expression defined in the function set. The leaf nodes of the tree are the index of the expression values of a gene. Expression transforms a string representation of chromosome to a functional meaningful construct. Thus the chromosome, after expression, resembles a forest of trees representing the ETs generated by each gene.

A GEP chromosome maintains multiple branches, each of which serves as the right hand side of the differential/difference equation. These ETs representing-complex mathematical functions are evolved from one time-step to next. Each equation uses a distinct program. Each ET in an chromosome is linked by using the summation operator to determine the goodness of fit in terms of absolute error in expression after evolution.

The model incorporates an effect of indirect coupling during the evolution process using a undirected matrix known as the coupling matrix of gene-gene interactions.

The coupling matrix is evolved along with the evolution of the right hand side of the differential/difference equations. The overall fitness of each chromosome is defined as effect of direct coupling of the genes using the equations and indirect coupling using the coupling matrix. Presence of even a single motif in the coupling map adds to the advantage of the individual. A brute force method is applied in order to search the coupling map for presence of a bi-partite fan and feed forward motif, which are statistically relevant to genetic regulatory networks A list of one and two path lengths is searched in the topology of the coupling matrix.

A one path length is simply a sequence of two nodes connected linearly, while a two path length a sequence of three nodes connected in a linear fashion. Each pair of one path lengths are checked for connections similar to that of a bi-partite fan motif.

Similarly each of the two path lengths is checked for the connections similar to that of a feed forward loop motif. The fitness of each of the chromosome is calculated with respect to the goodness of fit in term of absolute error in expression after evolution, the presence of motifs which are statistically prevalent in the network and the stability of the network.

The time series is calculated using an fourth order Runge Kutta method, if the equations being evolved are differential equations. Other wise an iterative scheme is used in case of discovery of a difference equation. The chromosome which is closer to the target time series has the higher possibility to be selected and inherited in the next generation. When calculating the time series, some chromosomes may go overflow.

In this case the chromosomes fitness value gets so large that it gets weeded out from the population. The selection process allows the program to select chromosomes fit for evolution in the next generation. The chances of being selected for the next generation are completely depended on the fitness value of the chromosomes. Selection pressure determines the number of chromosomes, ranked according to their fitness values, that will be selected for replication in the next generation. During replication the chromosomes are dully copied in the next generation. The best chromosome of each generation is always carried over in the next generation (elitism). The selection process is followed by a variation in the structure of the chromosomes and the coupling matrix.

The structure of chromosomes is varied using various genetic operators. The genetic operators act on any section of the chromosome or a pair of chromosomes, but maintain the structural organization of the chromosome intact. The mutation operator causes a change by either, replacing a function or terminal in the chromosomes head with another (function or terminal) or by replacing a terminal in the chromosomes tail with another.

A sequence of the symbols is selected from the chromosome as the Insertion Sequence (IS) transposon. A copy of this transposon is made and inserted at any position in the head of a randomly selected gene, except the first position. A sequence with as many symbols as the IS element is deleted at the end of the head of the target gene. All Root Insertion Sequence (RIS) transposition elements start with a function and thus are chosen from among the sequence of heads. During RIS transposition the whole head shifts to accommodate the RIS element. The last symbols of the head equivalent in the number to the RIS string are deleted. The gene transposition operators transpose an entire gene from one location to another allowing duplication of the genes within the chromosome.

The one-point recombination operator uses a pair of chromosomes for the sake of variation. The chromosomes are spliced at random point in both the chromosome and the material downstream of the splitting point is exchanged between the two chromosomes. A similar approach is followed in the two point recombination where there are two splitting points instead of one. In a gene recombination operation, two genes are randomly chosen between two chromosomes and exchanged. Interplay between these genetic operators beings about an excellent source of genetic diversity in the population while maintaining the syntactical correctness of the programs being evolved.

The coupling matrix is changed along with the structure of the chromosome during the variation process. The coupling matrix is varied by turning the interaction between two genes on or off. If the interaction between two genes is on, it is turned off and vice versa. The number of neighbors of each of the genes thus gets changed due to this variation bringing about a significant change in the fitness of the chromosome.

The chromosomes are evolved for a fixed number of generations or until the fitness of chromosomes has not converged to a desired value. The chromosomes are ranked according to the fitness and stability criteria and the output is a set of networks maintained by these chromosomes.

Pruning/Ranking Connections

While using the evolutionary algorithm for inference, we include the penalties for conformance with other data sets in the fitness function. These penalties can be included in two ways for each data set. We can reward a particular individual in a population for every link in the individual which is in accordance with a given secondary data set and punish it if a link which ought to be there for the given secondary set is not present.

The total penalty for the individual given that data set is then composed of penalties for the links. In the other approach, we only reward and do not have any punishment. This is helpful in cases where the secondary data set is not on the same footing as the primary one in our confidence and we would like to consider only additional support a link in primary set gets from this data set and not the punishment. The over all penalty from a secondary data is also assigned a weight before incorporating it in the fitness function. This weight can be chosen by the experimenter to suit the particular context.

The advantage of this approach is that we can prune or strengthen the connection based on additional evidence. Each connection can be assigned a weight which tells us about how reliable it is given a number of data sets.

The primary data set itself can be a network previously inferred using some other methodology. In such a case, present invention can be used to validate it given additional data and remove any connection which is not consistent with additional data.

We claim:

1. A computer-implemented method to combine diverse experimental data sets and to infer a network out of such data, the method comprising the steps of:
   a. designating one of the data sets as primary and the rest as secondary,
   b. analyzing the secondary data sets to obtain a connection matrix out of the secondary data sets by using statistical methods comprising R-square measures, clustering, correlation studies and mutual information measures,
   c. evolving a population of models and choosing a model from the population by proposing a population of plural nodes and connections from representation and representing the population by strings of characters and associated trees, with the string representation including characters representing data entities as well as a choice of mathematical operators,
   d. evaluating the values of the associated trees by integrating or iterating differential or difference equations along branches of the trees for a candidate in the population,
   e. assigning a fitness measure to each candidate based on i) presence of known motifs in the network, ii) stability of the network as evaluated by a linear stability analysis, iii) statistical measure of correlations in the data and iv) consistency with the prior known connections in the network, and
   f. incorporating penalties obtained from connection matrices in step b) into the fitness measure to arrive at an initial guess population consistent with the connections from the experimental data sets.

2. The computer-implemented method of claim 1 where the data sets include gene expression data, protein interaction data and gene knockout experiment data.

3. The computer-implemented method of claim 1, wherein the data sets include data representative of experimental data, knowledge from the literature, patient data, clinical trial data, compliance data; chemical data, medical data, or hypothesized data.

4. The computer-implemented method of claim 1, wherein the data sets include multivariate, parameterized data including, but not restricted to time series data, financial data, email or other social network data, simulated data from a known network structure.

5. The computer-implemented method of claim 1, wherein the primary datasets are gene expression data, gene expression profiles with varying environmental conditions including time, protein interaction data and gene knockout experiment data.

6. The computer-implemented method of claim 1, wherein the secondary data sets are location analysis, protein-protein interaction, two hybrid data, and pathway information or transcription factor relations obtained from sequence or previous knowledge represented in form of a connection matrix.

7. The computer-implemented method of claim 1, further comprising the step of interchanging the configuration of primary and secondary data sets and obtaining a consensus network.

8. The computer-implemented method of claim 1, wherein the method further comprises the step of computer-implemented tuning of various inference or evolution parameters.

9. The computer-implemented method of claim 1, wherein the tuning of various inference or evolution parameters is computer-implemented.

10. The computer-implemented method of claim 1, wherein the steps are performed iteratively for a specified number of iterations or until a specified accuracy threshold is reached.

11. The computer-implemented method of claim 7, wherein the method further comprises the step of computer-implemented tuning of various inference or evolution parameters.

12. The computer-implemented method of claim 8, wherein the tuning of various inference or evolution parameters is computer-implemented.

* * * * *